United States Patent [19]

Masel

[11] 4,040,188
[45] Aug. 9, 1977

[54] ORTHODONTIC NECK BAND INCLUDING SAFETY STRAP

[76] Inventor: Jacob J. Masel, 3021 Darnell St., Philadelphia, Pa. 19154

[21] Appl. No.: 639,757

[22] Filed: Dec. 11, 1975

[51] Int. Cl.² ............................................. A61C 7/00
[52] U.S. Cl. .................................................. 32/14 D
[58] Field of Search ................. 32/14 R, 14 D, 14 E, 32/20, 21, 14 A, 14 B, 14 C

[56] References Cited

U.S. PATENT DOCUMENTS

| 3,036,380 | 5/1962 | Martinek et al. | 32/14 D |
|---|---|---|---|
| 3,526,035 | 9/1970 | Armstrong | 32/14 D |
| 3,903,604 | 9/1975 | Snead | 32/14 D |

*Primary Examiner*—Russell R. Kinsey
*Assistant Examiner*—Robert P. Swiatek
*Attorney, Agent, or Firm*—Weiser, Stapler & Spivak

[57] ABSTRACT

A safety orthodontic neck band including a resilient band connected at its ends with an extra-oral orthodontic appliance for tensioning purposes when the orthodontic appliance is applied to the teeth of a patient. The apparatus also includes a non-extensible safety band which is co-extensive with the resilient neck band and overlies the resilient neck band in close proximity. The safety band also connects to the ends of the orthodontic appliance to thereby prevent accidental or unwanted movement of the extra-oral orthodontic appliance forwardly relative to the teeth of the patient. The orthodontic neck band including safety strap of the present invention functions to prevent forward movement of the orthodontic appliance and at the same time continuously tensions the appliance during all periods of use.

15 Claims, 5 Drawing Figures

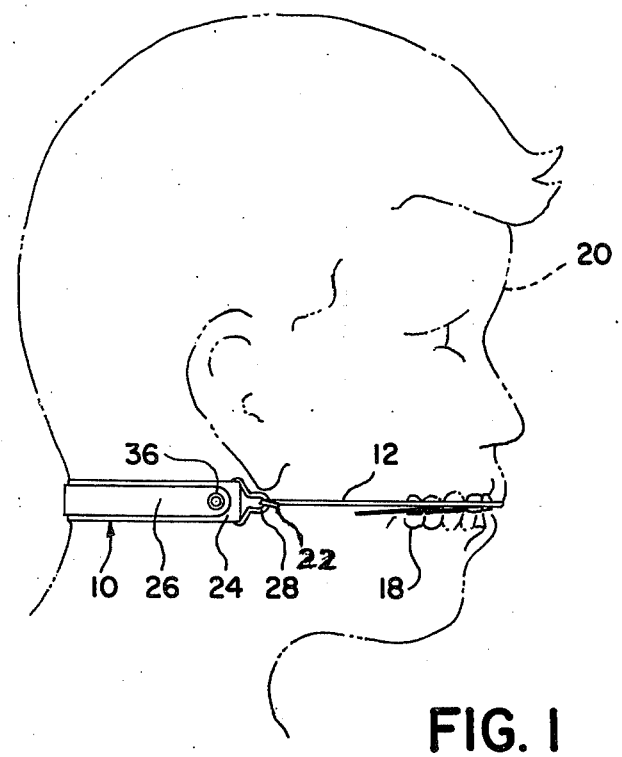
FIG. 1
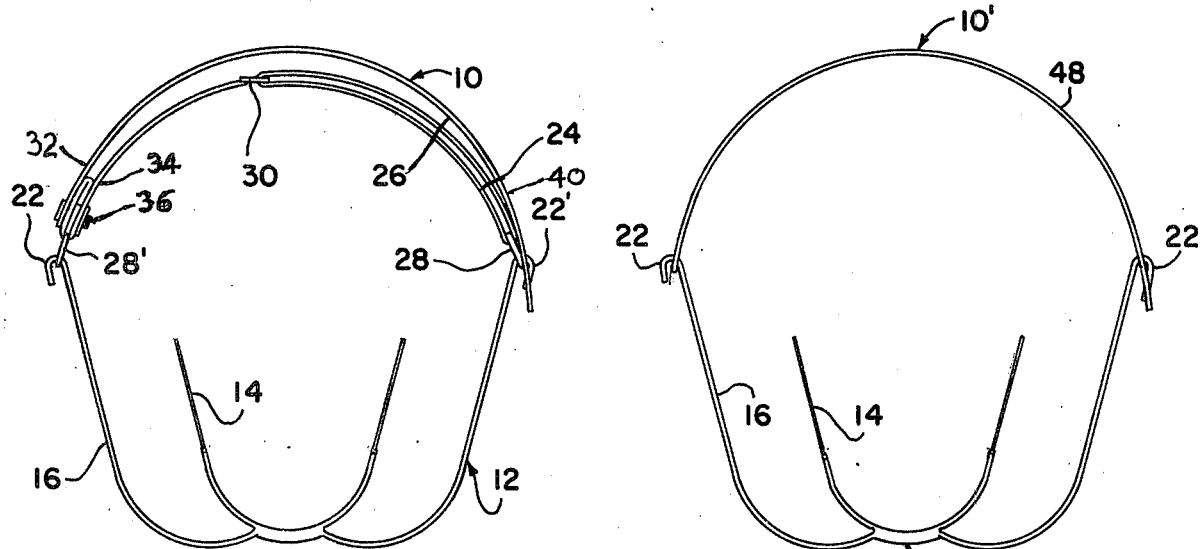
FIG. 3
FIG. 5

ORTHODONTIC NECK BAND INCLUDING SAFETY STRAP

BACKGROUND OF THE INVENTION

This application is directed to orthodontic appliances in general, and more particularly, to devices for applying external tension to extra-oral orthodontic devices.

Extra-oral orthodontic devices are normally of the type in which the teeth are placed in traction through the use of a tensioning means connected to a neck band or to a head band which is normally worn on the patient's neck or head. Traction is applied to the teeth through an outer face bow and tensioning means usually include two hooks, one on each side of the mouth. The hooks extend back along the sides of the face and are secured to the neck band or head band by the tensioning means. If the neck band extends around the back of the neck from ear to ear, it is generally referred to as a cervical strap. If the head band extends around the back of the head from ear to ear, it is usually referred to as an occupital strap. In the past, the tensioning device used to connect the hooks to the neck band or head band has commonly been an elastic or other resilient band arrangement capable of continuously biasing the outer face bow.

Types of prior art resilient neckor head bands are shown for example in U.S. Pat. Nos. 2,874,468, 3,765,093, 3,512,257 and 3,186,089. The prior art resilient neck band constructions have been used essentially for tensioning the orthodontic appliances and continuously act to pull the inside bow rearwardly in the mouth of the patient.

Recently, it has been found that the very tensioning means which acts to pull the inside bow rearwardly in the mouth of the patient presents a considerable hazard when mischievious or negligent persons unthinkingly act to pull the face bow forwardly in the mouth of the patient. In fact, there is at least one reported occurrence wherein the face bow was pulled forwardly against the bias of the neck band and then released to cause a portion of the inside bow to pierce the eye of the patient thereby causing grevious injury.

SUMMARY OF THE INVENTION

The present invention relates generally to neck bands for orthodontic face bows, and more particularly is directed to a combination orthodontic neck band including a safety strap.

The present invention in one embodiment incorporates a resilient neck band for use in attaching to the hooks of an orthodontic face bow appliance which serves to pull the inside bow rearwardly in the mouth of the patient. A cooperating, non-extensible band overfits the resilient band and also connects to the orthodontic appliance at the rear hooks thereof.

In operation, the orthodontic appliance is fitted in the mouth of the patient and tension is applied through use of the resilient neck band or head band in conventional manner. Once the parts have been properly positioned and the neck or head band tensioned as desired, the non-extensible band is then applied across the back of the neck or head in overfitting relationship to the resilient neck band. The non-extensible member is affixed at both ends to the hooks of the orthodontic appliance without interference with the tension applied by the resilient neck band. The non-extensible band thereby has no effect on the functional operation of the orthodontic device.

The non-resilient or non-extensible neck band or head band serves to prevent any unwanted forward movement of the orthodontic device in the mouth of the patient even if the device is pulled intentionally or negligently forwardly. The non-resilient band firmly connects to the orthodontic device hooks at the remote rear ends and thereby prevents any unwanted forward motion without interference with the normal bias and function of the resilient portion of the combination orthodontic neck band.

It is therefore an object of the present invention to provide an improved combination orthodontic neck band including safety strap of the type set forth.

It is another object of the present invention to provide a novel orthodontic neck band including safety strap incorporating a resilient member and a non-extensible member in cooperative arrangement.

It is another object of the present invention to provide a novel orthodontic neck band including safety strap incorporating construction suitable to continuously bias an orthodontic device rearwardly within the mouth of a patient and simultaneously to prevent forward movement of the orthodontic device relative to the mouth of the patient.

It is another object of the present invention to provide a novel orthodontic neck band including safety strap wherein the safety strap is provided with non-resilient body construction whereby the safety strap connects to the ends of an orthodontic appliance to prevent unwanted forward movement of the orthodontic appliance relative to the mouth of a patient.

It is another object of the present invention to provide a novel orthodontic neck band for use with an extraoral orthodontic device of the type including a non-extensible constructionto prevent unwanted forward movement of the device.

It is another object of the present invention to provide a novel orthodontic neck band including safety strap that is simple in construction, inexpensive in manufacture and trouble-free when in use.

Other objects and a fuller understanding of the invention will be had by referring to the attached drawings, wherein like reference characters refer to similar parts throughout and in which :

BRIEF DESCRIPTION OF THE DRAWINGS

FIG. 1 is a side elevational view of an orthodontic neck band including a safety strap showing the invention in use.

FIG. 3 is a top plan view of the device illustrated in FIG. 2.

FIG. 5 is a top plan view of the construction of FIG. 4.

DESCRIPTION OF THE PREFERRED EMBODIMENT OF THE INVENTION

Figure 2:
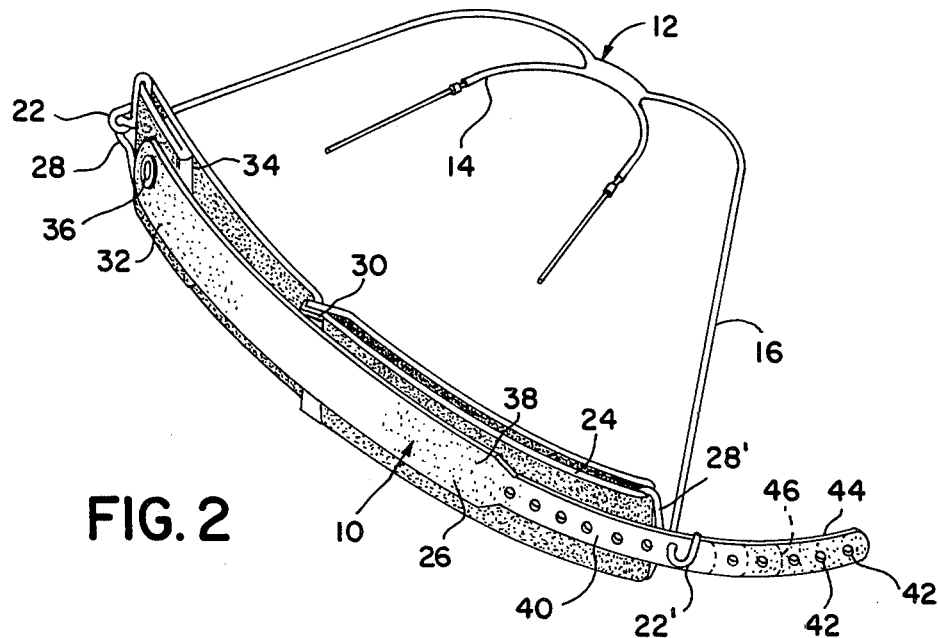
FIG. 2 is an isometric view of the invention as applied to an orthodontic extra-oral arch.

Although specific terms are used in the following description for the sake of clarity, these terms are intended to refer only to the particular structure of my invention selected for illustration in the drawings, and are not intended to define or limit the scope of the invention.

Referring now to the drawings, in FIG. 1 is shown an orthodontic neck band including safety strap generally designated 10 in use with a conventional orthodontic face bow or extra-oral arch 12. As illustrated in FIGS. 2 and 3, the orthodontic face bow 12 is conventional in design and incorporates a usual outer bow 16 and inner bow 14. The ends of the inside bow 14 are employed to conventionally apply rearward traction in well known manner to the teeth 18 of a patient 20. The outside bow 16 terminates rearwardly in a pair of spaced hooks 22, 22' and the safety strap 10 is applied as tensioning means by attaching the strap to the rear hooks 22, 22'.

Referring to FIGS. 2 and 3, and referring particularly to the safety strap construction, the orthodontic neck band including safety strap 10 comprises a resilient neck band 24 and a cooperating non-extensible or non-resilient safety strap 26. The resilient neck band 24 may be conventionally fabricated of elasticized fabric suitable for orthodontic face bow tensioning purposes. The resilient neck band 24 is conventionally fabricated of a length of relatively narrow elastic fabric having a metallic or plastic connector 28, 28' affixed at each end. The resilient neck band 24 is folded upon itself and about an adjustment clip 30, in conventional manner to permit easy length adjustment to thereby vary the tension of the resilient neck band 24 of the combination safety strap 10. The resilient neck band 24 is connected at the rear hooks of the face bow 12 in the usual manner by applying a connector 28 or 28' to each of the rear hooks 22, 22'. The bias of the resilient neck or head band 24 applied at the rear hooks 22, 22' pulls the extra-oral device rearwardly to apply traction forces to the patient's teeth 18.

The non-extensible band 26 may be affixed at one end 32 thereof to one end 34 of the resilient band 24 or to the connector 28 in permanent manner such as by employing a grommet or rivet 36 to affix the parts together at their respective ends 32, 34. Optionally, the band 26 and the resilient band 24 could be separate and be individually connected to the rear hooks 22, 22' of the face bow 12. The free end or adjustment end 40 is formed with an elongated adjustment tab which is punched or otherwise provided with a plurality of longitudinally spaced holes 42 for connection to a rear hook 22, 22' of the face bow 12. The non-extensible band 26 may be fabricated of any suitable thin, flexible, non-extensible material such as plastic, flexible metal or other suitable material.

In use, the extra oral arch 12 is applied to the mouth of the patient 20 in the usual manner with the outer bow 16 extending rearwardly along the sides of the patient's face. The orthodontic neck band including safety strap 10 is then applied to one rear hook 22 of the extra oral arch or face bow 12 by engaging the band connector 28 with the face bow hook 22. With the neck band engaged at one end thereof, the combination neck band and safety strap is then drawn across the back of the neck or the back of the head of the patient 20 and then the second connector 28' is affixed to the second rear hook 22' of the face bow 12 in conventional manner. The desired tension is then applied by shortening or lenthening the resilient neck band or head band 24 as necessary at the adjustment clip 30 until the desired bias and fit is provided. With the parts thus arranged, the adjustment end 40 of the non-resilient band 26 is applied over the second hook 22' of the face bow 12 until one of the holes 42 in the adjustment end overfits the end of the second hook 22'. The hole 42 which aligns with the second hook 22' is then applied over the hook 22' to thereby anchor the non-extensible band 26 to the extra oral arch 12. In this manner, both the resilient band portion 24 and the non-extensible band portion of the combination safety strap are firmly engaged at both ends thereof to the rear hooks 22, 22' of the orthodontic face bow 12. The unused end 44 of the adjustment end 40 extends beyond the face bow hook, as best seen in FIG. 2.

The unused end 44 of the non-resilient band 26 can then be removed by serving along a suitable cut line 46 to thereby trim the end to the desired length. In this manner, the desired tension to the orthodontic face bow 12 can be readily applied by utilizing the resiliency of the resilient neck band 24. Additionally, the non-extensible band 26 is affixed to both ends of the face bow 12 to thereby prevent any accidental or unwanted pulling of the face bow 12 fowardly relative to the face of the patient 20 by overcoming the bias of the resilient neck band 24.

Figure 4:
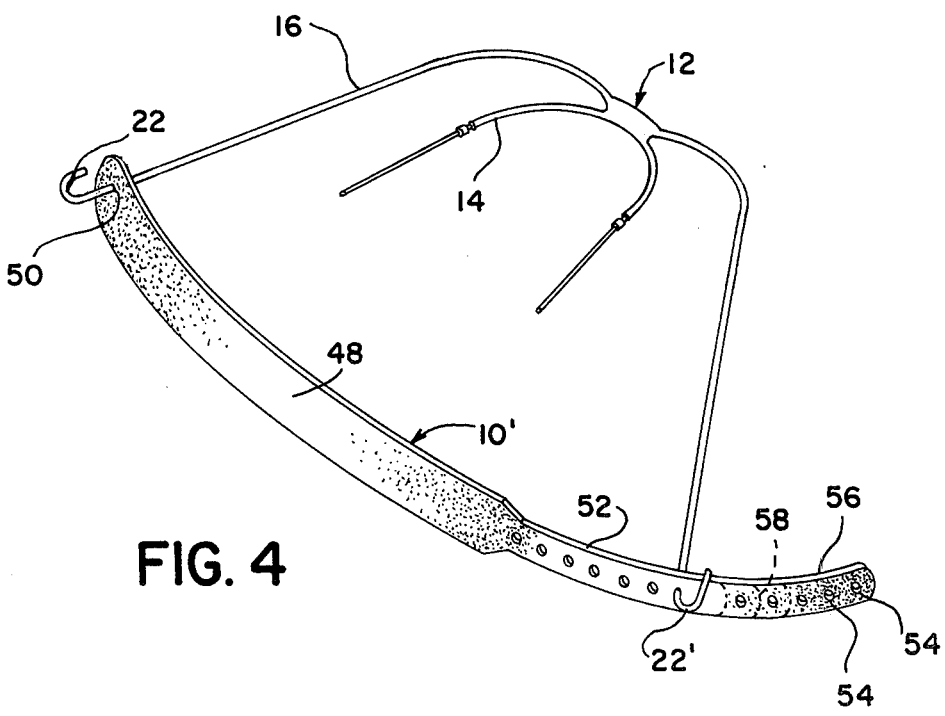
FIG. 4 is an isometric view similar to FIG. 2 showing a modified safety strap construction.

Referring now to FIGS. 4 and 5, I showed a modified orthodontic neck band including safety strap construction 10' which is applied to a usual orthodontic face bow or extra oral arch 12 at the rearwardly positioned hooks or attaching terminals 22, 22' thereof. In this embodiment, only a single length of non-extensible neck or head band 48 is employed. The non-extensible neck band 48 may be fabricated of any suitable, thin, non-extensible material such as plastic, flexible metal or the like. As best seen in FIG. 4, the non-resilient or non-extensible neck band 48 is formed at one end thereof with a hole 50 of suitable size to overfit and engage one rear hook 22 of the orthodontic face bow 12. The free end 52 of the band 48 is provided with a plurality of longitudinally spaced holes 54 of suitable size to engage the second rear hook 22' of the face bow 12. When the device has been fitted and a suitable hole 54 has been utilized for connection to the face bow 12 at the second rear hook 22' thereof, the unused end 56 may be conveniently served by cutting the end along one of the laterally spaced cut lines 58.

In order to use the modified orthodontic neck band including safety strap 10' of the present invention, the hole 50 at one end of the non-extensible neck band 48 is affixed to the orthodontic face bow at one rear hook 22 thereof in the usual manner. The band 48 is then applied across the back of the neck or head of the patient in conventional manner until the second end 52 overfits the second rear hook 22' of the face bow 12. With the parts thus positioned, suitable tension is applied to the face bow as necessary for orthodontic purposes and then one of the holes 54 which is suitably positioned to apply desired tension to the teeth of the patient 20 is affixed to the second end 22' of the orthodontic face bow 12 in such a manner as to maintain tension. As previously stated, the neck or head band 48 is non-extensible in nature and accordingly, unwanted or accidental foward pulling pressure applied upon the face bow 12 will not move the face bow forwardly relatively to the teeth 18 of the patient. In this manner, the non-resilient neck band 48 serves additionally as a safety strap so that the face bow cannot be accidentally pulled. After the desired hole 54 has been applied to the second rearward hook 22' of the face bow 12, the unused end 56 of the band 48 can be conveniently removed by cutting the free end along any of the cut lines 58 available for that purpose.

Although I have described the present invention with reference to the particular embodiments herein set forth, it is understood that the present disclosure has been made only by way of example and that numerous changes in the details of construction may be restored to without departing from the spirit and scope of the invention. Thus, the scope of the invention should not be limited by the foregoing specification, but rather only by the scope of the claims appended hereto.

I claim:

1. In an orthodontic device, the combination of
   a face bow, said face bow comprising attaching terminals;
   a resilient band attached to the face bow at at least one terminal,
   said resilient band tensioning the face bow; and
   a non-extensible band overlying the resilient band,
   the non-extensible band being connected to the face bow to prevent movement of the face bow in a direction tending to extend the band.

2. The orthodontic device of claim 1 wherein the resilient band and the non-extensible band are substantially coextensive in length.

3. The orthodontic device of claim 1 wherein the resilient band the non-extensible band each have two ends, and wherein the bands are connected at one respective end thereof.

4. The orthodontic device of claim 1 wherein resilient band and non-extensible band are removably connected to the said terminals of the face bow.

5. The orthodontic device of claim 1 wherein the non-extensible band includes means to connect to the terminal.

6. The orthodontic device of claim 5 where in the means to connect comprises an opening.

7. The orthodontic device of claim 5 wherein the means to connect comprises a plurality of longitudinally spaced openings.

8. The orthodontic device of claim 7 wherein one of said openings is employed to connect the non-resilient band to the face bow at the sane terminal whereat the resilient band is attached.

9. The orthodontic device of claim 1 wherein the non-extensible band connects to the face bow at both terminals thereof.

10. In a band for use with an orthodontic device of the type including a face bow which terminates rearwardly in a pair of terminals, the improvement which comprises
    a resilient band being attached to the face bow and extending between the terminals; and
    a non-extensible band overlying the resilient band, said non-extensible band being attached to the face bow and extending substantially between the terminals,
    whereby the resilient band serves to pull the face bow toward the bands and the non-extensible band serves to prevent movement of the face bow in a direction away from the bands.

11. The band of claim 10 wherein the resilient band comprises means to adjust the length of the resilient band.

12. The band of claim 10 wherein the resilient band and the non-extensible band each have two ends and wherein the respective bands are connected together at one end thereof.

13. The band of claim 10 wherein the non-extensible band comprises means to adjust the length of non-extensible band.

14. The band of claim 13 wherein the resilient band comprises means to adjust the length of the resilient band.

15. The band of claim 13 wherein the means to adjust comprises a plurality of longitudinally spaced openings.

* * * * *